(12) United States Patent
Rao et al.

(10) Patent No.: US 6,503,552 B1
(45) Date of Patent: Jan. 7, 2003

(54) ADDING FLAVIDIN TO A COMPOSITION AS AN ANTI-OXIDANT

(75) Inventors: Lingamallu Jagan Mohan Rao, Mysore (IN); Guddadarangavvanahally Krishnareddy Jayaprakasha, Mysore (IN); Kunnumpurath Kurian Sakariah, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/491,824

(22) Filed: Jan. 26, 2000

(51) Int. Cl.$^7$ .................. A23B 4/14; G01N 21/75; C07D 311/78
(52) U.S. Cl. ............... 426/541; 549/384; 436/166; 426/73
(58) Field of Search .............. 426/541, 73; 549/384; 436/166

(56) References Cited

PUBLICATIONS

Hedalgo 1994 Phyto Chemistry 37(6) 1585–1587.*
Rao 1989 Phyto Chemistry 28(11) 3031–3034.*
Majumder 1982 Phyto Chemistry 21(11) 2713–2716.*
Sachdev 1986 Phyto Chemistry 25(2) 499–502.*
Majumder 1993 Phyto Chemistry 32(2) 439–444.*
Anuradha 1994 Phyto Chemistry 35(1) 273–274.*
Majumder 1997 Phyto Chemistry 44(1) 167–172.*

* cited by examiner

Primary Examiner—Carolyn Paden
(74) Attorney, Agent, or Firm—Renner, Otto, Boisselle & Sklar, LLP

(57) ABSTRACT

The present invention relates to use of natural flavidin compound (2,7-dihydroxy 9,10-dihydrophenanthro-4,5 bcd-pyran) as an antioxidant in compositions comprising flavidin and other additives.

1 Claim, 1 Drawing Sheet

ADDING FLAVIDIN TO A COMPOSITION AS AN ANTI-OXIDANT

TECHNICAL FIELD

This present invention relates to use of natural flavidin as an antioxidant.

BACKGROUND OF THE INVENTION

Antioxidants play a crucial role in preventing or delaying autoxidation and have attracted a lot of attention as food additives. The deterioration of food with time, results from its biological nature largely and is inevitable. During the production, processing, distribution, storage preceding and even during actual consumption food undergoes various modes of deterioration that involve biological changes by microbes as well as chemical changes. The latter is represented by enzymatic and non-enzymatic oxidation of lipids and phenolic substance, which cause undesirable changes in flavor, appearance, physical character, nutritional value and toxicity. Deoxygenation, airtight packing, and other techniques have solved some of these problems, but the role of antioxidants as either food constituents or as additives cannot be overlooked. Both synthetic and natural antioxidants are widely used in many food products.

The area of natural antioxidants has been developing since the past decade, mainly because of the increasing limitations on the use of synthetic antioxidants and enhanced public awareness of health issues. In general, natural antioxidants are preferred by consumers because they are considered environmental friendly. Commercial antioxidants are generally synthetic compounds and there has been a growing interest in replacing them with natural ingredients due to possible toxicity of synthetic antioxidants (*J. Food Sci.*, 42, 1102, 1977) as shown by clinical studies (Toxicological aspects of antioxidants used as food additives, *In-Food Antioxidants;* Hudson, B. J. F., Ed.; Elsevier; London, 1990; p. 253). Further, the use of some common synthetic antioxidants such as butylated hydroxy anisole (BHA) and butylated hydroxytolune (BHT) has become a controversial issue because of adverse toxicological data (Food antioxidants, edited by Madhavi, Despande and Salunkhe, Marcel Dekker, Inc., New York 1995, p. 267). The use of natural antioxidants in food is limited due to the lack of knowledge about their molecular compositions, the content of active compounds in the raw materials and the availability of relevant toxicological data. Hence, evaluation of the antioxidative activity of naturally occurring substances has been of interest in recent years (*Nahrung*, 1996, 40, 261). Currently, the use of some naturally occurring antioxidants in preventive and therapeutic medicine is gaining popularity. Rosemary and Marjoram are known to contain powerful antioxidants. But these are not indigenous to India.

A literature survey revealed that, there is no report on the antioxidant activity of phenanthropyran type of compounds which are abundantly found in a few genera of family Orchidaceae. The family of Orchidaceae is one of the largest families of flowering plants. Orchids are most facinating by reason of their diversity and specialization in floral and regulative features. Members of Orchidaceae are widely distributed in all parts of the world with the greatest concentration being in tropics. About 860 species belonging to 132 genera grow in various regions of India. Particularly, the foot hill areas of Himalayas, western and eastern ghats are rich sources of orchids. Subtribes viz Dendrobium, Bulbophyllinae and Coelogyninae are reported to possess 9,10-dihydro-5H phenanthro-(4,5 bcd)-pyrans and pyrones. Flavidin (2,7-dihydroxy 9,10-dihydrophenanthro-4,5 bcd-pyran) is found in many of these subtribes, mainly in the species of Coelogyne genus (*Phytochemistry*, 28, 3031, 1989). The applicants, during their study found that these compounds exhibit anti-oxidant properties.

SUMMARY OF THE INVENTION

Accordingly, the main object of the invention is to provide materials capable of being used as anti-oxidants in food compositions or food products.

Another objective is to provide food compositions that contain natural flavidin (2,7-dihydroxy 9,10-dihydrophenanthro-4,5 bcd-pyran) compounds as antioxidants for preservation of food products.

Yet another object is to provide methods for preservation of food products employing natural flavidin compounds of the invention.

BRIEF DESCRIPTION OF DRAWINGS

FIGS. 1(a) and 1(b) show the decrease in absorbance of β-carotene and linoleic acid. Different bleaching rates were observed for the flavidin and BHA.

DETAILED DESCRIPTION OF THE PREFERRED EMBODIMENTS

Figure 1A:
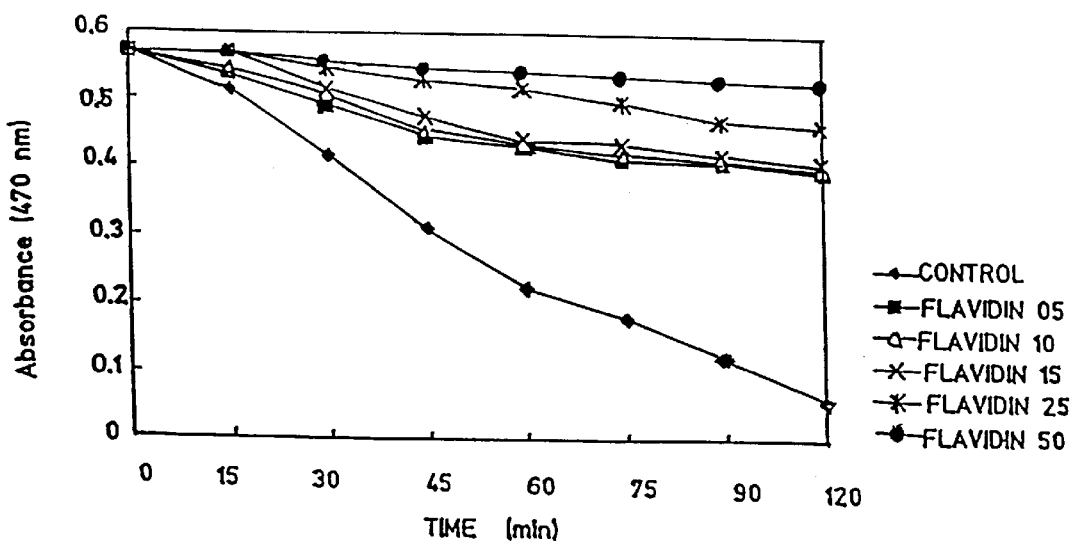
FIG. 1(a) and FIG. 1(b) represent the antioxidant activities of flavidin with different concentrations compared with BHA respectively. The controls (no additive) are decolorized within 120 min, indicating that rapid oxidation occurred. The addition of flavidin and BHA at different concentrations enhanced the bleaching time of β-carotene. Flavidin, at 10 ppm concentration showed 68.5% antioxidant activity and at 50 ppm showed maximum activity of 90.2% in 120 min.

In accordance with the above and other objectives, the invention provides natural flavidin (2,7-dihydroxy 9,10-dihydrophenanthro-4,5 bcd-pyran) compounds capable of being used as anti-oxidants in food compositions or food products. The invention also provides food compositions that contain natural flavidin as anti-oxidants for preservation of food products.

The structure of 2,7-dihydroxy 9,10-dihydrophenanthro-4,5 bcd-pyran is shown below in Formula (I).

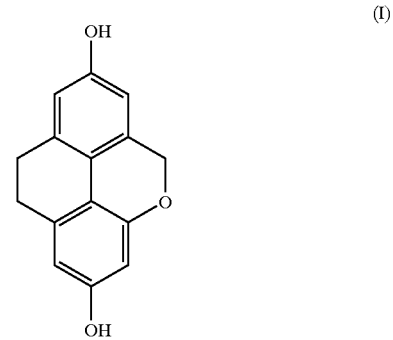

In an embodiment, the invention provides method of using natural flavidin 2,7-dihydroxy 9,10-dihydrophenanthro-4,5 bcd-pyran as an anti-oxidant in food compositions and preservatives, said method comprising the steps of adding natural flavidin to the food composition or preservatives.

In an embodiment, the invention provides natural flavidin exhibiting antioxidant activity wherein antioxidant activity of natural flavidin is evaluated by the method comprising the steps of:

a) isolating flavidin compound of formula (I) from a plant of genus Coelogyne, family Orchidaceae by conventional methods,
b) identifying the isolated compound as flavidin by conventional methods,
c) preparing an assay reagent of β-carotene in chloroform by adding linoleic acid and polyoxyethylene sorbitan monopalmitate,
d) removing chloroform at a temperature of about 40° C. under vacuum using a rotary evaporator,
e) diluting the resulting solution with triple distilled water,
f) diluting the mixed emulsion further with oxygenated water,
g) transferring aliquots of the reagent prepared into different tubes containing the compound (a) (flavidin) in evaluation,
h) preparing control of ethanol and emulsion from step (f),
i) measuring the optical density of all samples immediately and at specific intervals, and
j) evaluating the anti-oxidant property of flavidin in terms of bleaching β-carotene.

In an embodiment, the warming of polyoxyethylene sorbitan monopalmitate is effected in a water bath at a temperature of about 50° C.

In another embodiment, the incubation of tubes containing the reaction mixture as in step (g) is effected in water bath at a temperature of about 50° C.

In still another embodiment, flavidin compound at a concentration of 10 ppm showed 68.5% antioxidant activity.

In another embodiment, 25 ppm of flavidin compound showed 79% antioxidant activity.

In yet another embodiment, 50 ppm of flavidin compound showed 90.2% antioxidant activity.

In yet another embodiment, the antioxidant activity of flavidin was evaluated by a method comprising the steps of:

i) obtaining pure flavidin by isolating fractionating and identifying flavidin compounds from plant materials of Orchidaceae species and
ii) determining the antioxidant activity of said flavidin compound using β-carotene-linoleate system.

In an embodiment of present invention flavidin was isolated and purified by a method which comprises the following steps:

i) loading fractions containing flavidin (400 mg) impregnated Silica gel (mesh size 60–120) onto 5 g silica column and eluting with chloroform,
ii) eluting the first two fractions of 100 ml each containing minor compounds with 1 % MeOH in chloroform,
iii) evaporating the elute under vacuum to remove chloroform and getting the compound in crystallized form (150 mg), mp 210° C., and
iv) confirming the structure of flavidin and its chemical shifts by $^1$H NMR spectra to match to reported value (J.Nat.Prod., 45, 730, 1982).

In another embodiment of the present invention, evaluation of the antioxidant activity of flavidin has been carried out employing the procedure of Hiddgi et. al. (*Phytochem*, 37, 1585, 1994) with minor modifications said method comprises the following steps:

i) preparing assay reagent of β-carotene in chloroform by mixing linoleic acid and 200 mg of Tween 40 (polyoxyethylene sorbitan monopalmitate),
ii) warming polyoxyethylene sorbitan monopalmitate (Tween 40) at a temperature of about 50° C. in a water bath,
iii) removing chloroform from assay reagent at a temperature of about 40° C. under vacuum using a rotary evaporator,
iv) diluting the resulting solution with triple distilled water and mixing the resulting emulsion well for one minute,
v) further diluting the resulting emulsion with oxygenated water,
vi) transferring aliquots of the reagent as in step (v) into tubes containing 0.2 ml of desired amount of antioxidant in ethanol,
vii) keeping a control of 0.2 ml of ethanol and 4 ml of reagent as prepared in step (v).
viii) immediately taking optical density of all sample (t=0) and also taking the O.D at 15 min. interval for 2 hr. (t=120),
ix) incubating the tubes in water bath at a temperature of about 50° C. between each measurement taken, and
x) measuring the color till the color of β-carotene disappears.

In an embodiment of present invention flavidin was isolated as per procedure of Veerraju et al., (*Phytochemistry*, 28, 3031, 1989). The fraction containing flavidin was further purified by column chromatography. 200 mg of fraction containing flavidin was impregnated with silica gel (mesh size 60–120) (400 mg) and loaded onto a 5 g silica column and eluted with chloroform. First two fractions of 100 ml each contain other minor compounds, flavidin was eluted with 1% MeOH in chloroform. Eluates were evaporated under vacuum and crystallized from chloroform (150 mg), mp 210° C. The structure (I) of flavidin was confirmed by $^1$H NMR spectra and its chemical shifts were matched to reported values (*J.Nat.Prod.*, 45, 730, 1982).

The procedure of Hiddgo et al., (*Phytochemistry*, 37, 1585, 1994) was followed for testing of antioxidant activity of the flavidin with minor modification. The assay reagent was prepared as follows: 0.2 mg of β-carotene in 0.5 ml of chloroform was added to 20 mg of linoleic acid and 200 mg of Tween 40 (polyoxyethylene sorbitan monopalmitate) were mixed. Tween 40 was warmed in a water bath at 50° C. before use. The chloroform was removed at 40° C. under vacuum using a rotary evaporator. The resulting solution was immediately diluted with 10 ml of triple-distilled water and the emulsion was mixed well for 1 min. The emulsion was further diluted with 40 ml oxygenated water. Four ml aliquots of this reagent were transferred into different tubes containing 0.2 ml of the desired amount of antioxidant in ethanol. A control consisting of 0.2 ml of ethanol and 4 ml of emulsion was prepared. Optical density of all samples were taken immediately (t=0) and at 15 min intervals for 2 h (t=120). The tubes were placed in a water bath at 50° C. between measurements. All determinations were preformed in duplicate. Measurement of color was recorded until the color of β-carotene disappears.

All the reagents were prepared fresh before use. β-carotene and BHA were obtained from Sigma Chemical Co., (St. Louis, Mo.), linoleic acid and Tween 40 were obtained from Himedia Ltd. India. Silica gel (mesh size 60–120) and solvents used were of analytical grade and obtained from Merck, India.

UV-Visible spectra is measured using Genesys 5 UV-Visible spectrophotometer (Milton Roy, USA). $^1$H NMR spectra was recorded at 400 MHz on Bruker AMX 400FT instrument. TMS was used as internal standard.

The antioxidant activity (AA) of the isolated compound was evaluated in terms of bleaching the β-carotene using the formula of Hiddgo et al., (*Phytochemistry*, 37, 1585, 1994). $AA=100[1-(A_o-A_t)/(A°o-A°_t)]$ where $A_o$ and $A°$ are the absorbance measured at the beginning of the incubation for flavidin and the control, respectively, and $A_t$ and $A°_t$ are the absorbance measured in the presence and absence of the flavidin after incubation for 120 min.

Figure 1B:
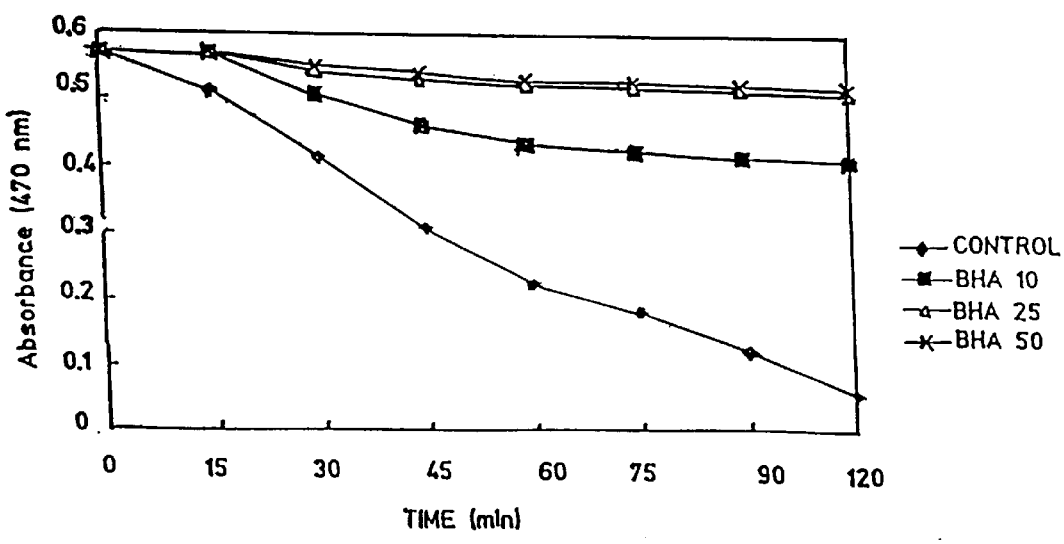

FIG. 1(*a*) and FIG. 1(*b*) represent the antioxidant activities of flavidin with different concentrations compared with BHA respectively. The controls (no additive) are decolorized within 120 min, indicating that rapid oxidation occurred. The addition of flavidin and BHA at different concentrations enhanced the bleaching time of β-carotene. Flavidin, at 10 ppm concentration showed 68.5% antioxidant activity and at 50 ppm showed maximum activity of 90.2% in 120 min. FIGS. 1(*a*) and 1(*b*) show the decrease in absorbance of β-carotene and linoleic acid. Different bleaching rates were observed for the flavidin and BHA.

The following examples are provided by way of illustrations only and therefore should not be construed to limit the scope of the present invention.

EXAMPLE 1

A β-carotene-linoleate emulsion was prepared as mentioned earlier. Four ml aliquots of this reagent were transferred into different tubes containing 0.2 ml (10 ppm) of the flavidin in ethanol. A control consisting of 0.2 ml of ethanol and 4 ml of emulsion was prepared. Optical density of all samples were taken immediately (t=0) and at 15 min intervals for 2 h (t=120) as mentioned earlier. The antioxidant activity of flavidin at 10 ppm was found to be 68.5%.

EXAMPLE 2

A β-carotene-linoleate emulsion was prepared as mentioned earlier. Four ml aliquots of this reagent were transferred into different tubes containing 0.2 ml (25 ppm) of the flavidin in ethanol. A control consisting of 0.2 ml of ethanol and 4 ml of emulsion was prepared. Optical density of all samples were taken immediately (t=0) and at 15 min intervals for 2 h (t=120) as mentioned earlier. The antioxidant activity of flavidin at 25 ppm was found to be 79%.

EXAMPLE 3

A β-carotene-linoleate emulsion was prepared as mentioned earlier. Four ml aliquots of this reagent were transferred into different tubes containing 0.2 ml (50 ppm) of the flavidin in ethanol. A control consisting of 0.2 ml of ethanol and 4 ml of emulsion was prepared. Optical density of all samples were taken immediately (t=0) and at 15 min intervals for 2 h (t=120) as mentioned earlier. The antioxidant activity of flavidin at 50 ppm was found to be 90.2%.

The above results showed that, 9,10-dihydrophenathropyrans could exhibit antioxidant properties that are comparable to commercial synthetic antioxidants.

What is claimed is:

1. A method of using natural flavidin (2,7-dihydroxy 9,10-dihydrophenanthro-4,5 bcd-pyran) as an anti-oxidant in a composition, said method comprising the steps of adding natural flavidin to the composition.

* * * * *